US012215204B2

United States Patent
Wakita et al.

(10) Patent No.: US 12,215,204 B2
(45) Date of Patent: *Feb. 4, 2025

(54) SILICONE RESIN-COVERED SILICONE ELASTOMER PARTICLES, ORGANIC RESIN ADDITIVE, AND OTHER USES

(71) Applicant: DOW TORAY CO., LTD., Tokyo (JP)

(72) Inventors: Mari Wakita, Ichihara (JP); Hiroko Taniguchi, Ichihara (JP); Takeshi Yoshizawa, Ichihara (JP)

(73) Assignee: DOW TORAY CO., LTD., Tokyo (JP)

( * ) Notice: Subject to any disclaimer, the term of this patent is extended or adjusted under 35 U.S.C. 154(b) by 756 days.

This patent is subject to a terminal disclaimer.

(21) Appl. No.: 16/955,221

(22) PCT Filed: Dec. 19, 2018

(86) PCT No.: PCT/JP2018/046703
§ 371 (c)(1),
(2) Date: Jun. 22, 2020

(87) PCT Pub. No.: WO2019/124418
PCT Pub. Date: Jun. 27, 2019

(65) Prior Publication Data
US 2020/0332124 A1    Oct. 22, 2020

(30) Foreign Application Priority Data
Dec. 20, 2017  (JP) .................................. 2017-243392

(51) Int. Cl.
*C08J 3/12*     (2006.01)
*A61K 8/891*    (2006.01)
(Continued)

(52) U.S. Cl.
CPC .............. *C08J 3/126* (2013.01); *A61K 8/891* (2013.01); *A61Q 1/12* (2013.01); *C08G 77/08* (2013.01);
(Continued)

(58) Field of Classification Search
CPC ......... C08G 77/38; C08J 3/24; C08J 2383/04; C08J 3/126; C08L 83/06; C08L 2312/08; C08L 83/14
See application file for complete search history.

(56) References Cited

U.S. PATENT DOCUMENTS 5,538,793 A   7/1996  Inokuchi et al.
5,756,568 A   5/1998  Morita et al.
(Continued)

FOREIGN PATENT DOCUMENTS

EP   3699235 A1   8/2020
FR   2972350 A1   9/2012
(Continued)

OTHER PUBLICATIONS

Machine assisted English translation of FR2972350A1 obtained from https://patents.google.com/patent on Aug. 18, 2021, 8 pages.
(Continued)

*Primary Examiner* — Timothy P Thomas
(74) *Attorney, Agent, or Firm* — WARNER NORCROSS + JUDD LLP

(57) ABSTRACT

Provided is a silicone resin-coated silicone elastomer particle that is superior in dispersibility into organic resins, in stress relaxation performance, and the like, and that has low dust scattering when mixing and thus is superior in ease of handling. Also provided is an organic resin additive, an organic resin, a coating composition, or a coating agent composition, and applications such as in cosmetic compositions, including the particle. The silicone resin-coated
(Continued)

silicone elastomer particle has a structure wherein at least two silicon atoms in a silicone elastomer particle are cross-linked through a silalkylene group with a carbon number between 4 and 20 where some or all of the surface thereof is coated with a silicone resin structured from siloxane units expressed by $SiO_{4/2}$.

19 Claims, 1 Drawing Sheet

(51) Int. Cl.
  *A61Q 1/12* (2006.01)
  *C08G 77/08* (2006.01)
  *C08G 77/12* (2006.01)
  *C08G 77/38* (2006.01)
  *C08J 7/04* (2020.01)
  *C08L 83/06* (2006.01)
  *C09D 183/06* (2006.01)
  *C09D 183/14* (2006.01)

(52) U.S. Cl.
  CPC ............ *C08G 77/12* (2013.01); *C08G 77/38* (2013.01); *C08J 7/0427* (2020.01); *C08L 83/06* (2013.01); *C09D 183/06* (2013.01); *C09D 183/14* (2013.01); *C08J 2383/05* (2013.01); *C08J 2383/14* (2013.01); *C08L 2312/08* (2013.01)

(56) References Cited

U.S. PATENT DOCUMENTS

| | | | |
|---|---|---|---|
| 5,928,660 | A | 7/1999 | Kobayashi et al. |
| 5,945,471 | A * | 8/1999 | Morita ............... B29B 9/16 524/588 |
| 5,948,469 | A | 9/1999 | Morita et al. |
| 2006/0084758 | A1 | 4/2006 | Morita |
| 2009/0052017 | A1 | 2/2009 | Sasaki |
| 2010/0112023 | A1 | 5/2010 | Inokuchi et al. |
| 2010/0112074 | A1 | 5/2010 | Inokuchi et al. |
| 2010/0203095 | A1 | 8/2010 | Inokuchi et al. |
| 2010/0203097 | A1 | 8/2010 | Tanaka |
| 2011/0110994 | A1 | 5/2011 | Inokuchi et al. |
| 2011/0117146 | A1 | 5/2011 | Inokuchi et al. |
| 2012/0121909 | A1 | 5/2012 | Kobayashi et al. |
| 2013/0040144 | A1 | 2/2013 | Inokuchi et al. |
| 2013/0090448 | A1 | 4/2013 | Inokuchi et al. |
| 2013/0095324 | A1 | 4/2013 | Inokuchi et al. |
| 2014/0322280 | A1 | 10/2014 | Inokuchi |
| 2019/0038520 | A1 | 2/2019 | Igarashi |
| 2019/0144612 | A1 * | 5/2019 | Hori ................ C08L 83/14 528/31 |
| 2020/0332124 | A1 | 10/2020 | Wakita et al. |

FOREIGN PATENT DOCUMENTS

| | | | |
|---|---|---|---|
| JP | H4348143 | A | 12/1992 |
| JP | H07196815 | A | 8/1995 |
| JP | H8109262 | A | 4/1996 |
| JP | H9208709 | A | 8/1997 |
| JP | H1036219 | A | 2/1998 |
| JP | H10175816 | A | 6/1998 |
| JP | 2000063674 | A | 2/2000 |
| JP | 2003226812 | A | 8/2003 |
| JP | 2004210944 | A | 7/2004 |
| JP | 2010132877 | A | 6/2010 |
| JP | 2010132878 | A | 6/2010 |
| JP | 2010180335 | A | 8/2010 |
| JP | 2011026469 | A | 2/2011 |
| JP | 2011102354 | A | 5/2011 |
| JP | 2011105663 | A | 6/2011 |
| JP | 2011168634 | A | 9/2011 |
| JP | 2011219547 | A | 11/2011 |
| JP | 2012517959 | A | 8/2012 |
| JP | 2013040241 | A | 2/2013 |
| JP | 2013087141 | A | 5/2013 |
| JP | 2014214263 | A | 11/2014 |
| WO | 2006098334 | A1 | 9/2006 |
| WO | 2007061032 | A1 | 5/2007 |
| WO | 2011002695 | A1 | 1/2011 |
| WO | 2017142068 | A1 | 8/2017 |
| WO | WO-2017191798 | A1 * | 11/2017 ............ A61K 8/891 |
| WO | 2019124418 | A1 | 6/2019 |

OTHER PUBLICATIONS

English translation of International Search Report for PCT/JP2018/046703 dated Mar. 12, 2019, 2 pages.
Machine assisted English translation of JPH08109262A obtained from https://patents.google.com/patent on Sep. 17, 2020, 17 pages.
Machine assisted English translation of JPH09208709A obtained from https://patents.google.com/patent on Sep. 17, 2020, 10 pages.
Machine assisted English translation of JPH1036219A obtained from https://patents.google.com/patent on Sep. 17, 2020, 11 pages.
Machine assisted English translation of JPH2003226812A obtained from https://patents.google.com/patent on Sep. 17, 2020, 7 pages.
Machine assisted English translation of JP2011168634A obtained from https://patents.google.com/patent on Sep. 17, 2020, 10 pages.
English translation of the International Search Report for PCT/JP2019/050182 dated Mar. 10, 2020, 3 pages.
Machine assisted English translation of JP2000063674A obtained from https://patents.google.com/patent on Sep. 29, 2021, 9 pages.
Machine assisted English translation of JP2011219547A obtained from https://patents.google.com/patent on Sep. 29, 2021, 10 pages.
Machine assisted English translation of WO2007061032A1 obtained from https://patents.google.com/patent on May 2, 2022, 9 pages.
"Silicones", Apr. 15, 2003 (Apr. 15, 2003), Encyclopedia of Polymer Science and Technology, Wiley, US, pp. 765-841, XP007918236.

* cited by examiner

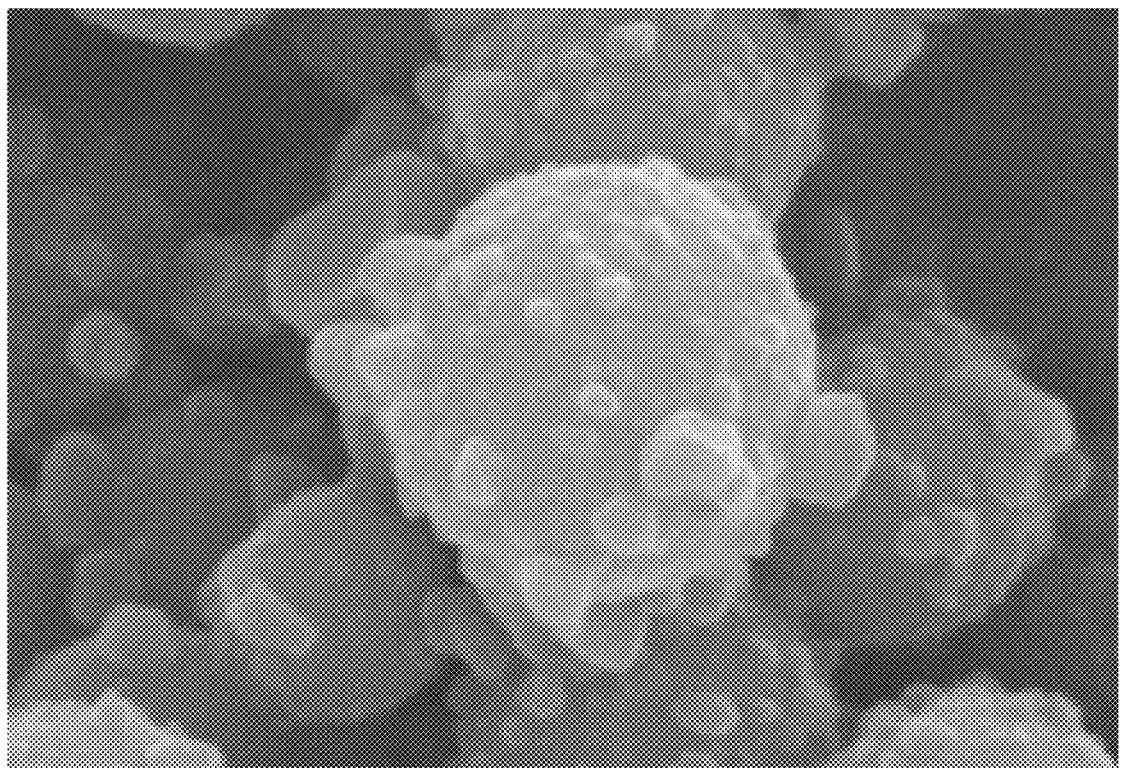

SILICONE RESIN-COVERED SILICONE ELASTOMER PARTICLES, ORGANIC RESIN ADDITIVE, AND OTHER USES

CROSS-REFERENCE TO RELATED APPLICATIONS

This application is the National Stage of International Appl. No. PCT/JP2018/046703 filed on 19 Dec. 2018, which claims priority to and all advantages of Japanese Appl. No. 2017-243392 filed on 20 Dec. 2017, the content of which is hereby incorporated by reference.

FIELD OF TECHNOLOGY

The present invention relates to a silicone resin-coated silicone elastomer particle that is dispersible into organic resins, such as epoxy resins, and the like, and, if desired, superior in stress relaxation, and also superior in ease of handling due to low dust when mixing. Moreover, the present invention relates to organic resin additives, and other applications, that include the silicone resin-coated silicone elastomer particle, and to a method for manufacturing the silicone resin-coated silicone elastomer particle.

PRIOR ART

Silicone elastomer particles are used as a control additive in cosmetics, coatings, inks, thermally curable organic resins, thermoplastic organic resins, and the like, and, in particular, are well suited for use as a thermally curable organic resin internal stress relaxing agent or an organic resin film surface lubricant. In particular, silicone elastomer particles have thermal durability and flexibility, deriving from the elastomer skeletons thereof, and thus are particularly well-suited as an internal stress relaxing agent in resin substrates for semiconductors, functional organic resin films, resin coatings thereon, and the like.

On the other hand, silicone elastomer particles are susceptible to electrostatic charging, and when added to a thermally curable organic resin tend to agglomerate, which has a negative effect on the uniformity of dispersion within the resin, and thus sometimes lack the performance desired in stress relaxing agents for organic resins after curing. Because of this, Patent Documents 1 through 4 (and Patent Document 3 in particular) propose a silicone composite particle wherein dispersibility, and the like, in organic resins is improved through coating the silicone particle surface with a silicone resin structured from silsesquioxane, expressed as $SiO_{3/2}$, and propose application thereof to an internal stress relaxing agent, cosmetic compositions, and the like. However, while these silicone composite particles improve the dispersibility into organic resin and stress relaxation when compared to mixing of silicone elastomer particles alone, the surfaces are coated with a silicone resin structure that is structured from silsesquioxane units, which tends to lead to dust, and adheres to containers (including interior bags made from organic resins such as vinyl), which tends to have a negative effect on the ease of handling. Moreover, there is still room for improvement with regard to, for example, oil absorption, and the like, and there is the need to further improve the feel as a raw material for cosmetics.

On the other hand, the present applicant has proposed a silicone particle as a silicone particle that has superior dispersibility, high lipophilicity, and a high storage stability, wherein the per-unit-mass silicon atom-bound hydrogen atom inclusion proportion, described in Patent Document 5, is low, and includes alkylene groups with carbon numbers between 4 and 20, which cure a cross-linkable composition for forming silicone particles that include alkenyl groups with between 4 and 20 carbon atoms, such as hexenyl groups. However, while the silicone particles have benefits, as a cosmetic raw material, of sufficient dispersibility, lipophilicity, and the like, there is still room for improvement in terms of performance as a cosmetic raw material that is superior in terms of dispersibility into organic resins, oil absorption, and feel in use.

On the other hand, the present applicant, and others, have proposed, in Patent Document 6 and Patent Document 7, cross-linked silicone particles, and the like, of a core/shell type, wherein the surface of a cross-linkable silicone particle is covered with a silicone compound that has a silicon atom-bound hydrolyzable group (siloxane, silane, or the like). However, in these documents there is no disclosure nor suggestion of coating, with a silicone resin structure that is structured from specific siloxane units, the surface of a cross-linkable silicone particle that includes specific silalkylene groups, nor of the technological effects thereof.

PRIOR ART DOCUMENTS

Patent Documents

[Patent Document 1] Japanese Unexamined Patent Application Publication 2010-132878
[Patent Document 2] Japanese Unexamined Patent Application Publication 2011-105663
[Patent Document 3] Japanese Unexamined Patent Application Publication 2011-168634
[Patent Document 4] Japanese Unexamined Patent Application Publication 2011-102354
[Patent Publication 5] International Patent Application Publication WO 2017/191798
[Patent Document 6] Japanese Unexamined Patent Application Publication 2003-226812
[Patent Publication 7] International Patent Application Publication WO 2006/098334

BRIEF DESCRIPTIONS OF THE DRAWINGS

FIG. 1 is an electron microscope photograph of the silicone resin-coated silicone elastomer particle according to a first embodiment.

SUMMARY OF THE INVENTION

Problem Solved by the Present Invention

An object of the present invention is to provide a silicone resin-coated silicone elastomer particle, and manufacturing method thereof, that can be manufactured easily on an industrial scale, that has superior dispersibility into a curable organic resin, such as an epoxy resin, and superior oil absorption, and that has superior ease of handling due to having reduced dust during mixing, when compared to a conventional silicone resin-coated silicone. Moreover, an object of the present invention is to provide the silicone resin-coated silicone elastomer particles as an organic resin additive that is superior in functions such as stress relaxation characteristics, and the like, and in other applications. Moreover, an object of the present invention is to provide an organic resin that includes the silicone resin-coated silicone elastomer particles. Additionally, an object of the present invention is to provide a cosmetic composition that includes these silicone resin-coated silicone elastomer particles, and that has superior feel in use.

Means for Solving the Problem

As a result of earnest research in order to solve the problems set forth above, the present inventor arrived at the present invention through the discovery that the problems set forth above can be solved through the use of a silicone resin-coated silicone elastomer particle having a structure wherein some or all of the surface thereof is coated with a silicone resin structured from siloxane units expressed by $SiO_{4/2}$ and wherein, in the silicone elastomer particle, at least two silicon atoms are cross-linked by a silalkylene group with a carbon number between 4 and 20. The silicone resin-coated silicone elastomer particles can be produced easily through a manufacturing method that includes a step for coating, with a silicone resin that is a hydrolyzate of a tetraalkoxysilane, the surface of a silicone elastomer particle that was produced through, for example, an aqueous suspension or a spray dryer, or the like.

The present inventors arrived at the present invention through the discovery that it is possible to solve the problems set forth above through the use of the silicone resin-coated silicone elastomer particles as an organic resin additive and in other applications, and through an organic resin including the same.

That is, the object of the present invention is achieved through:

[1] A silicone resin-coated silicone elastomer particle having a structure wherein at least two silicon atoms in a silicone elastomer particle are cross-linked through a silalkylene group with a carbon number between 4 and 20 where some or all of the surface thereof is coated with a silicone resin structured from siloxane units expressed by $SiO_{4/2}$.

The object of the present invention may be achieved through a layered body having the following structure:

[2] A silicone resin-coated silicone elastomer particle as set forth in [1], wherein: the amount of coating by the silicone resin structured from the silicone units expressed by $SiO_{4/2}$ is in a range of between 5.0 and 40.0 parts by weight in respect to 100 parts by weight of the silicone elastomer particle.

[3] A silicone resin-coated silicone elastomer particle as set forth in [1] or [2], wherein: the average primary particle diameter measured through a laser diffraction/scattering method is between 0.5 and 20 μm.

[4] A silicone resin-coated silicone elastomer particle as set forth in any one of [1] through [3], wherein: the JIS-A hardness that is measured for the silicone elastomer particles in a state wherein they are not coated with the silicone resin, through curing, in a sheet shape, the cross-linkable composition for forming the silicone elastomer particles, prior to curing thereof, is in a range between 10 and 80.

[5] A silicone resin-coated silicone elastomer particle as set forth in any one of [1] through [4], wherein: the silalkylene groups included in the silicone elastomer particles are substantially only silalkylene groups with carbon numbers between 4 and 8, where the inclusion proportion of silalkylene groups with carbon numbers of 3 and below is less than 5 mass % in respect to the silicone elastomer particle.

[6] A silicone resin-coated silicone elastomer particle as set forth in any one of [1] through [5], wherein: the silicone resin of the silicone elastomer particle surface is made up substantially from a hydrosilate of a tetraalkoxysilane where the inclusion proportion of siloxane units other than siloxane units expressed by $SiO_{4/2}$ is less than 5 mass % in respect to the silicone resin.

[7] A silicone resin-coated silicone elastomer particle as set forth in any one of [1] through [6], wherein: the inclusion proportion of silicon atom-bound hydrogen is no greater than 300 ppm, per unit mass.

[8] A silicone resin-coated silicone elastomer particle as set forth in any one of [1] through [7], wherein:
a cross-linkable composition for forming a silicone elastomer particle, prior to curing thereof, for a silicone elastomer particle in a state wherein it is not coated with silicone resin, is a cross-linkable composition that includes:
(a) an organopolysiloxane having at least two alkenyl groups, with a carbon number between 4 and 20, per molecule;
(b) an organohydrogen polysiloxane having at least two silicon atom-bound hydrogen atoms per molecule; and
(c) a hydrosilylation reaction catalyst, wherein:
the mole ratio of the alkenyl group inclusion proportion (Alk) of the component (a) and the silicon atom-bound hydrogen atom inclusion proportion (H) of the component (b) is in a range of:
H/Alk=0.7 through 1.2.

Moreover, the object of the present invention is achieved through a composition that includes the silicone resin-coated silicone elastomer particle described above, and the use thereof in specific applications. Specific examples thereof are as follow.

[9] An organic resin additive that includes a silicone resin-coated silicone elastomer particle as set forth in any one of [1] through [8].

[10] An organic resin that includes a silicone resin-coated silicone elastomer particle as set forth in any one of [1] through [8].

[11] A cured organic resin composition that includes a silicone resin-coated silicone elastomer particle as set forth in any one of [1] through [8].

[12] A coating composition or coating agent composition that includes a silicone resin-coated silicone elastomer particle as set forth in any one of [1] through [8].

[13] A cosmetic composition that includes a silicone resin-coated silicone elastomer particle as set forth in any one of [1] through [8].

Moreover, the object according to the present invention is achieved through a method for manufacturing the silicone resin-coated silicone elastomer particle, described above.

[14] A method for manufacturing a silicone resin-coated silicone elastomer particle as set forth in any one of claim 1 through 8, including the following steps (I), (II), and (III):
Step (I):
a step for preparing a cross-linkable composition having:
(a) an organopolysiloxane having at least two alkenyl groups, with a carbon number between 4 and 20, per molecule;
(b) an organohydrogen polysiloxane having at least two silicon atom-bound hydrogen atoms per molecule; and
(c) a hydrosilylation reaction catalyst, wherein:
the mole ratio of the alkenyl group inclusion proportion (Alk) of the component (a) and the silicon atom-bound hydrogen atom inclusion proportion (H) of the component (b) is in a range of:
H/Alk=0.7 through 1.2
emulsifying it in water, and curing in the presence of the (c) hydrosilylation reaction catalyst, to produce a spheroidal silicone elastomer particle;

Step (II):
a step for coating with a silicone resin that is a hydrolysate of a tetraalkoxysilane, a surface of a silicone elastomer particle of Step (I); and Step (III):
a step for using mechanical means to crush the silicone resin-coated silicone elastomer particles (including agglomerations) obtained in Step (II) to produce silicone resin-coated silicone elastomer particles with an average primary particle diameter of between 0.5 and 20 µm, measured through a laser diffraction/scattering method.

Effects of the Invention

The silicone resin-coated silicone elastomer particles according to the present invention can be manufactured easily on an industrial scale, and have superior dispersibility into curable organic resins, such as epoxy resins, and superior oil absorption, and superior ease in handling due to low dust during mixing, when compared to a conventional silicone resin based coated silicone, and thus can be used well as an organic resin additive that is superior in functions such as stress relaxation characteristics, and in other applications. Moreover, the silicone resin-coated silicone elastomer particles according to the present invention have superior uniformity of dispersion into curable organic resins, such as epoxy resins, and superiority in handling operations, and thus enable the efficient provision of epoxy resins, and the like, that are superior in stress relaxation characteristics, and the like, on an industrial scale. Moreover, cosmetics that have a superior feel in use can be provided through a cosmetic composition that includes the silicone resin-coated silicone elastomer particles according to the present invention.

MOST PREFERRED MODE FOR CARRYING OUT THE PRESENT INVENTION

The silicone resin-coated silicone elastomer particles according to the present invention, and, in particular, applications thereof that include an organic resin additive, along with a manufacturing method thereof, and an organic resin, a coating/coating agent, and a cosmetic composition that includes the same, will be explained in detail below.

The silicone resin-coated silicone elastomer particles according to the present invention have a structure wherein at least two silicon atoms in a silicone elastomer particle are cross-linked through a silalkylene group with a carbon number between 4 and 20 where some or all of the surface thereof is coated with a silicone resin structured from siloxane units expressed by $SiO_{4/2}$. Such particles can be produced through preparing silicone elastomer particles that have, per molecule, a structure that is cross-linked through silalkylene groups with carbon numbers between 4 and 20, and coating the surfaces thereof with a silicone resin structured from siloxane units wherein the hydrolysis condensation product of a tetraalkoxysilane, or the like, is expressed by $SiO_{4/2}$. When, for convenience, the term "silicone elastomer particle" is used, this refers to a silicone elastomer particle prior to coating or forming a composite through silicone resin.

[Silicone Elastomer Particles Prior to Coating]

First the silicone elastomer particles have a structure wherein, within the particle, at least two silicon atoms are cross-linked by a silalkylene group with a carbon number between 4 and 20. Preferably this type of silalkylene cross-linking structure is formed through causing a hydrosilylation reaction of an alkenyl group with a carbon number between 4 and 20 and a silicon atom-bound hydrogen atom, between different siloxane molecules. In the present invention, preferably the silalkylene group that cross-links between a silicon atom within the siloxane that structures the silicone elastomer particle and another silicon atom is a silalkylene group with a carbon number between 4 and 16, where, more preferably, this carbon number is in a range between 4 and 8, where 6 (that is, a hexylene group) is particularly preferred.

Here, from the perspective of being able to disperse into the organic resin the silicone resin-coated silicone elastomer particles that are ultimately produced, and the perspective of oil absorption, preferably the silicone elastomer particles substantially do not include, within the particles, silalkylene groups of a carbon number of 3 or less. Here "substantially do not include" is that the proportion with which silalkylene groups of a carbon number of 3 or below are included in the particle is less than 5 mass % in respect to the silicone elastomer particle, and preferably less than 3 mass %, and particularly preferably less than 1 mass %, where most preferably the amount of raw materials that are added intentionally and that provide silalkylene groups with a carbon number of 3 or less is zero, that is, 0 mass %. If silalkylene groups with a carbon number of 3 or less, introduced through a hydrosilylation reaction with vinyl groups, or the like, were to exist within the particle, the technological effect of the present invention might be incomplete.

There is no particular limitation on the average primary particle diameter of the silicone elastomer particle according to the present invention prior to coating with the silicone resin, but in the case of an organic resin additive that is added for the purpose of relaxing stress in an organic resin, preferably the average primary particle diameter, measured using a laser diffraction scattering method, is between 0.4 and 19 µm. These silicone elastomer particles provide silicone resin-coated silicone elastomer particles with an average primary particle diameter of between 0.5 and 20 µm, when ultimately measured using a laser diffraction scattering method, after further coating the surfaces thereof with a silicone resin structured from siloxane units that are expressed by $SiO_{4/2}$, followed, if necessary, by grading. Note that the average primary particle diameter of the particles after coating, of course, is greater than that of the silicone elastomer particles prior to coating.

The shapes of the silicone elastomer particles according to the present invention may be, for example, spheroidal, spherical, elliptical, or irregular, where spheroidal and spherical are particularly preferred. Spheroidal silicone elastomer particles can be produced easily through a method wherein a form of an aqueous solution, described below, is produced, and dried using a vacuum dryer, a hot air circulating oven, or a spray dryer.

From the perspective of technological effects such as the feel in use as a cosmetic raw material, relaxation of stress when mixed into an organic resin, prevention of tackiness, and the like, the silicone elastomer particles according to the present invention are elastomer particles that have elasticity, and preferably are particles wherein, when the cross-linkable composition for forming the silicone elastomer particles, prior to curing, is cured into a sheet shape and measured with a JIS A hardness meter, as specified in JIS K6301, will be in a range between 10 and 80. If the JIS-A hardness of the rubber sheet, measured after curing in a sheet shape the cross-linkable composition for forming the silicone elastomer particles, is within the aforementioned range, cohesiveness of the silicone elastomer particles produced will be suppressed thoroughly, making it easy to produce a feeling of fluidity, dispersibility, silkiness, smoothness, and softness, and, additionally, the selection of the JIS-A hardness, described above, can improve the stress relaxing properties when mixed into an organic resin, and will also have superiority in ease of handling after silicone resin coating. Moreover, the feeling of use of a cosmetic coated can be improved through mixing in the particles after silicone resin coating. Note that the silicone resin coating silicone elastomer particles according to the present invention, when used in a stress relaxing agent for an organic resin, has a JIS-A hardness of between 30 and 80, where the use of silicone elastomer particles wherein this is in a range of between 50 and 80 is particularly preferred.

The silicone elastomer particles according to the present invention further should have an inclusion proportion of silicon atom-bound hydrogen of no greater than 300 ppm, per unit mass. The silicon atom-bound hydrogen inclusion proportion more preferably is no greater than 250 ppm, and even more preferably no greater than 200 ppm. Moreover, no greater than 150 ppm is more preferred, and no greater than 100 ppm is even more preferred, and no greater than 50 ppm is even more preferred, and no greater than 20 ppm is even more preferred. In the silicone elastomer particles according to the present invention, if there were too much silicon atom-bound hydrogen, cross-linking reactions with the other reactive functional groups that remain within the silicone elastomer particles would advance, which would produce cohesion in the silicone elastomer particles or silicone resin-coated silicone elastomer particles as time progresses. Moreover, in the present invention, the production of flammable hydrogen gas as time elapses when these particles are stored is suppressed through reducing the silicon atom-bound hydrogen in the silicone elastomer particles so that no problems will arise such as swelling of the containers or ignition, so there will be the benefit of safety in handling when the silicone resin-coated silicone elastomer particles produced are used as an organic resin additive or in other applications.

Note that the method for measuring silicon atom-bound hydrogen in the silicone elastomer particles typically is a method that uses gas chromatography (the headspace method) after contact with alkali. For example, an ethanol solution of potassium hydroxide with a 40% concentration is added with equal amounts, in respect to unit mass, to the silicone elastomer particles, and after resting for one hour, the hydrogen gas that is produced up until the reaction endpoint is trapped, enabling identification through quantification through headspace gas chromatography, where the details thereof are disclosed in, for example, Patent Document 5, described above.

[Cross-Linkable Composition for Silicone Elastomer Particle Formation]

The silicone elastomer particles described above have a structure wherein at least two silicon atoms per molecule are cross linked by a silalkylene group with a carbon number between 4 and 20, and can be cured through a hydrosilylation reaction of a cross-linkable composition that includes the following components:

(a) an organopolysiloxane having at least two alkenyl groups, with a carbon number between 4 and 20, per molecule;

(b) an organohydrogen polysiloxane having at least two silicon atom-bound hydrogen atoms per molecule; and (c) a hydrosilylation reaction catalyst.

The component (a) is an organopolysiloxane having at least two alkenyl groups, with a carbon number between 4 and 20, per molecule, where there is no particular limitation on the structure thereof, and the structure may be of one or more types selected from straight-chain types, cyclic types, network types, and straight-chain types having partial branches, and straight-chain organopolysiloxanes are particularly preferred. The viscosity of this component (a) preferably is a viscosity that enables dispersion of the cross-linkable composition, described above, into water, or a viscosity range that enables dispersion in a spray dryer, or the like. Specifically, preferably it is in a range of between 20 and 100,000 mPa·s, and particularly preferably in a range of between 20 and 10,000 mPa·s, at 25° C.

From the perspective of oil absorbency and dispersibility of the silicone elastomer particles, preferably the component (a) is a straight-chain organopolysiloxane wherein the inclusion proportion of dimethyl siloxane units expressed by the formula: —(CH$_3$)$_2$SiO— is no less than 90 mol % of all siloxane units other than the siloxane units that are the molecule terminators. Similarly, from the perspective of oil absorbency of the silicone elastomer particles produced and of improving contact point damage in electronic components, and the like, that are equipped with the resin components after compounding, preferably the cyclic or straight organopolysiloxanes that have a low degree of polymerization (polymerization of between 3 and 20) have been removed, through stripping, or the like, from the component (a) in advance.

The alkenyl groups with a carbon number between 4 and 20 in component (a) may be, for example, butenyl groups, pentenyl groups, hexenyl groups, heptenyl groups, octenyl groups, nonenyl groups, decenyl groups, undecenyl groups, dodecenyl groups, tridecenyl groups, tetradecenyl groups, pentadecenyl groups, hexadecenyl groups, heptadecenyl groups, octadecenyl groups, nonadecenyl groups, icosenyl groups, or the like. From the perspective of reactivity and the perspective of cohesiveness, the carbon numbers of the alkenyl groups are between 4 and 16, and preferably in a range of between 4 and 8, and the use of a hexenyl group, which is an alkenyl group with a carbon number of 6, is particularly preferred. Moreover, preferably the alkenyl groups are on the ends of the molecular chains of the organopolysiloxanes, but they may instead be on side chains, or may be on both. As groups other than alkenyl groups that may be bonded to silicon atoms there are: alkyl groups such as methyl groups, ethyl groups, propyl groups, butyl groups, and the like; cycloalkyl groups such as cyclopentyl groups, cyclohexyl groups, and the like; aryl groups such as phenyl groups, tolyl groups, xylyl groups, and the like; aralkyl groups such as benzyl groups, phenethyl groups, 3-phenyl propyl groups, and the like; and non-substituted or substituted monofunctional hydrocarbon groups such as halogenated alkyl groups such as 3-chloropropyl groups, 3,3,3-trifluoropropyl groups, and the like.

Preferably component (a) is a straight-chain organopolysiloxane expressed by Chemical Formula (1) below:

[CHEMICAL FORMULA 1]

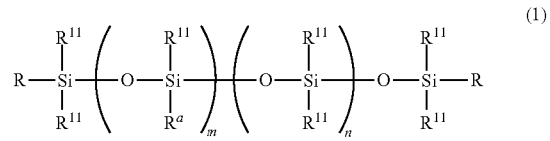

In Formula (1), $R^1$ 1 is, for each independently, an alkyl group with a carbon number of between 1 and 20 (for example, a methyl group, or the like) or an aryl group with a carbon number of between 6 and 22 (for example, a phenyl group, or the like), either non-substituted or substituted with a halogen atom, or a hydroxyl group, and, in industry, preferably is a methyl group or a phenyl group. Ra is an alkenyl group with a carbon number of between 4 and 20, and preferably is a hexenyl group. R is a group expressed by $R^1$ 1 or Ra. m is a number that is no less than 0, and n is a number that is no less than 1. Note that m, n, and R are numbers such that the inclusion proportion of the vinyl ($CH_2=CH-$) parts in the alkenyl groups with carbon numbers between 4 and 12 in the organopolysiloxane molecule expressed by Formula (1), above, will be between 0.5 and 3.0 mass %, and numbers such that the viscosity of the component (a) at 25° C. will be between 20 and 10,000 mPa·s.

Preferably component (a) is an organopolysiloxane having a hexenyl group on both ends of the molecular chain and on a side chain, expressed by Chemical Formula (2), below.

[CHEMICAL FORMULA 2]

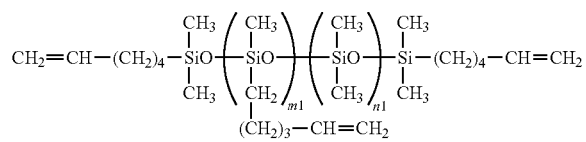

(2)

(In Formula (2), m1 is a number that is no less than 0 and each n1 is a positive number, where m1 is a number with which the inclusion portion of the vinyl ($CH_2=CH-$) part in the hexenyl groups ($-(CH_2)_4CH=CH_2$) in the molecule expressed by Formula (2) will be in a range between 0.5 and 3.0 mass %, and more preferably in a range of between 1.0 and 2.0 mass %. Moreover, m1+n1 is a number in a range such that the viscosity of the organopolysiloxane expressed by Formula (2), above, at 25° C. will be no less than 20 mPa·s, and, more preferably, between 100 and 500 mPa·s.)

Preferably the (b) organohydrogen polysiloxane having at least two silicon atom-bound hydrogen atoms per molecule is a cross-linking agent for component (a) and has at least three silicon atom-bound hydrogen atoms per molecule, where there is no particular limitation on the bonding positions of the hydrogen atoms within the molecule.

As organic groups, rather than hydrogen atoms, that are bonded to silicon atoms that are included in the component (b) there are, for example, alkyl groups such as methyl groups, ethyl groups, propyl groups, butyl groups, and octyl groups, where methyl groups are preferred. Moreover, the molecular structure of the organohydrogen polysiloxane of the component (b) may be a straight-chain type, a branched type, or a branched cyclic type, or combinations of more than one of the above. Note that the numbers of silicon-bound hydrogen atoms in a molecule are averages for all molecules.

The viscosity of component (b) at 25° C. is between 1 and 1000 mPa·s, and more preferably between 5 and 500 mPa·s. This is because there would be a tendency for the component (b) to evaporate from the cross-linkable composition in which it is included if the viscosity of the component (b) at 25° C. were less than 1 mPa·s, and the curing time for the cross-linkable composition including such a component (b) would be too long, and it could cause curing defects, if greater than 1000 mPa·s. There is no particular limitation on such a component (b) and it may be, for example, a copolymer of methyl hydrogen siloxane with a dimethyl siloxane blocked on both ends with trimethyl siloxy groups, a copolymer of methyl hydrogen siloxane and a dimethyl siloxane blocked on both ends with the methyl hydrogen siloxy groups, a dimethyl polysiloxane blocked on both ends with dimethyl hydrogen siloxy groups, a methyl hydrogen polysiloxane blocked on both ends with trimethylsiloxy groups, a cyclic methyl hydrogen polysiloxane, a copolymer of dimethylsiloxane with a cyclic methyl hydrogen siloxane, or the like.

Here preferably the H/Alk value that is the mole ratio of the alkenyl group inclusion proportion (Alk) of component (a) and the silicon atom-bound hydrogen atom inclusion proportion (H) of component (b) (=the reaction ratio in the hydrosilylation reaction), is in a range of between 0.7 and 1.2. Preferably the lower limit for this H/Alk is no less than 0.80, no less than 0.85, no less than 0.90, and no less than 0.95, where the upper limit is no greater than 1.15, and more preferably no greater than 1.10, or no greater than 1.05. If the upper limit for the H/Alk were greater than the values set forth above, there would be a tendency for non-reacted silicon atom-bound hydrogen atoms to remain after the reaction, and, conversely, if the H/Alk upper limit were less than the values described above, there would be a tendency for non-reacted alkenyl groups to remain after the reaction. Because these are the curing reactive groups, if large amounts thereof were to remain within the particles, this would cause cross-linking reactions between particles with the passage of time, which could result in cohesion between the silicone elastomer particles or silicone resin-coated silicone elastomer particles produced, or in dispersion defects, and, additionally, if there were residual reactive hydrogen atoms, this could cause the production of flammable hydrogen gas with the passage of time. Particularly preferably, with H/Alk values in the range of between 0.9 and 1.1, and particularly, near to 1.0, the curing reactive groups will be consumed completely, terminating the cross-linking reaction, which can suppress effectively cohesion between particles over time.

Component (c) is the hydrosilylation reaction catalyst, a catalyst that promotes the addition reaction (hydrosilylation reaction) between silicon atom-bound hydrogen atoms and the silicon atom-bound alkenyl groups that exist within the cross-linkable composition that is described above. Preferably the hydrosilylation reaction catalyst is a hydrosilylation reaction catalyst that includes a platinum-based metal, and, specifically, may be, for example, chloroplatinic acid, alcohol-modified chloroplatinic acid, an olefin complex of a chloroplatinic acid, a complex of chloroplatinic acid and a ketone, a complex of chloroplatinic acid and a vinyl siloxane, platinum tetrachloride, a platinum ultra-powder, solid platinum carried on an alumina or silica carrier, platinum black, an olefin complex of platinum, an alkenyl siloxane complex of platinum, a carbonyl complex of platinum, or a platinum-based catalyst that is a thermoplastic organic resin powder, such as, for example, a methyl methacrylate resin, a polycarbonate resin, a polystyrene resin, a silicone resin, or the like, that includes these platinum-based catalysts. In particular, complexes of chloroplatinic acid with divinyltetramethyldisiloxane, complexes of chloroplatinic acid with tetramethyltetravinylcyclotetrasiloxane, platinum divinyltetramethyldisiloxane complexes, platinum tetramethyltetravinyl chlorotetrasiloxane complexes, and other platinum alkenyl siloxane complexes can be used preferentially. Note that non-platinum-based metal catalysts, such as, for example, iron, ruthenium, iron/cobalt, and the like, may be used instead as the catalyst for promoting the hydrosilylation reaction.

The amount of component (c) to add to the cross-linkable composition should be a catalytic amount, where normally it should be an amount such that the amount of platinum-based metal included in the component (c) is in a range of between 1 and 1000 ppm in respect to the total mass of the cross-linkable composition, described above, where an amount such that this amount of platinum-based metal will be in a range of between 5 and 500 ppm is even more preferred. Note that the amount of platinum metal in the silicone elastomer particles may be reduced through the method proposed by the present inventor in Japanese Unexamined Patent Application Publication 2014-122316.

The timing with which composition (c) is added to the cross-linkable composition may be selected depending on the method for forming the silicone elastomer particles, and may be through addition into the composition in advance, or in a form wherein it is supplied from a spray line that is different from that for component (a) or component (b), and adding to either and mixing during spraying. Similarly, when through an aqueous suspension wherein the silicone elastomer particles are formed through emulsification in water, it may be added in advance to the cross-linkable composition, or an emulsifying compound that includes component (c) may be added separately into the water.

The cross-linkable composition described above may include a curing inhibiting agent that is typical with a hydrosilylation reaction inhibiting agent. This curing retarding agent may be, for example, an acetylene-based compound, and enyne compound, an organic nitrogen compound, an organic phosphorous compound, or an oxime compound. As specific compounds there are, for example, alkene alcohols such as 2-methyl-3-butyn-2-ol, 3,5-dimethyl-1-hexyne-3-ol, 3-methyl-1-pentyn-3-ol, 2-phenyl-3-butyn-2-ol, 1-ethynyl-1-cyclohexanol (ETCH), and the like; enyne compounds such as 3-methyl-3-trimethylsiloxy-1-butyne, 3-methyl-3-trimethylsiloxy-1-pentyne, 3,5-dimethyl-3-trimethylsiloxy-1-hexyne, 3-methyl-3-pentene-1-yne and 3,5-dimethyl-3-hexene-1-yne, and the like; and alkenyl siloxanes such as 1-ethynyl-1-trimethylsiloxycyclohexane, bis(2,2-dimethyl-3-butynoxy) dimethylsilane, methyl (tris (1,1-dimethyl-2-propynyloxy)) silane, 1,3,5,7-tetramethyl-1,3,5,7-tetravinylcyclotetrasiloxane and 1,3,5,7-tetramethyl-1,3,5,7-tetrahexenylcyclotetrasiloxane. The amount thereof to be added is in a range of between 0.001 and 5 parts by weight per 100 parts by weight of component (a), but may be designed as appropriate depending on, for example, the type of retarding agent used, the characteristics and amount of the hydrosilylation reaction catalyst used, and the like.

Preferably the cross-linkable composition substantially does not include, and particularly preferably completely excludes, organopolysiloxanes having alkenyl groups with carbon numbers of three or less, in addition to the component (a). This is because the oil absorbency, and the uniform dispersibility into organic resins, of the silicone resin-coated silicone elastomer particles that are ultimately produced would be inadequate with a composition wherein cross-linked products would be produced with silalkylene groups with carbon numbers of three or less, derived from alkenyl groups having these low carbon numbers, if they were to exist at 5 mass % or more within the particles.

The cross-linkable composition may include components other than the components described above in a range wherein the technological effect of the present invention is not lost. For example, it may include organic solvents such as: aliphatic hydrocarbons such as n-hexane, cyclohexane, n-heptane, and the like; aromatic hydrocarbons such as toluene, xylene, mesitylene, and the like; ethers such as tetrahydrofuran, dipropylether, and the like; silicones such as hexamethyldisiloxane, octamethyltrisiloxane, decamethyltetrasiloxane, and the like; esters such as ethyl acetate, butyl acetate, propylene acetate glycol monomethyl ether, and the like; and ketones such as acetone, methyl ethyl ketone, methylisobutyl ketone, and the like; non-reactive organopolysiloxanes (including linear or cyclic organopolysiloxanes which have low viscosities between about 0.5 and 10 mPa·s at 25° C.), such as polydimethyl siloxane or polydimethyldiphenyl siloxane, and the like; oxidation inhibitors such as those that are phenol-based, quinone-based, amine-based, phosphor-based, phosphide-based, sulfur-based, thioether-based, and the like; optical stabilizing agents such as those that are triazole-based, benzophenone-based, and the like; flame retarding agents such as those that are phosphoric acid ester-based, halogen-based, phosphor-based, antimony-based, and the like; antistatic agents comprising cationic surface activating agents, anionic surface activating agents, or nonionic surface activating agents, and the like; dyes; pigments; and so forth.

[Formation of the Silicone Elastomer Particles]

The method for forming the silicone elastomer particles used in the cross-linkable composition for forming the silicone elastomer particles, described above, may be a method that includes steps for preparing the cross-linkable composition described above, emulsifying it in water, curing in the presence of the (c) hydrosilylation reaction catalyst, and producing spheroidal silicone elastomer particles.

In this method, silicone elastomer particles can be obtained through emulsifying, in a surface activating agent aqueous solution, the cross-linkable composition for forming the silicone elastomer particles, followed by curing. Moreover, the particle size can be adjusted easily through adjusting the diameters of the emulsified particles. The surface activating agent may be nonionic, anionic, cationic, or betaine-based, for example. The particle sizes of the silicone elastomer particles produced will vary depending on the type of surface activating agent and the inclusion proportion thereof. To prepare silicone elastomer particles with small particle sizes, preferably the amount of added surface activating agent is in a range of between 0.5 and 50 parts by weight in respect to 100 parts by weight of the cross-linkable composition. On the other hand, in order to prepare silicone elastomer particles with a large particle size, preferably the amount of the surface activating agent added is in a range of between 0.1 and 10 parts by weight in respect to 100 parts by weight of the cross-linkable composition. Note that the amount of water added as the dispersing agent preferably is in a range of between 20 and 1500 parts by weight, or between 50 and 1000 parts by weight, in respect to 100 parts by weight of the cross-linkable composition.

Preferably an emulsifier is used in order to uniformly disperse, into water, the cross-linkable composition for forming the silicone elastomer particles, described above. The emulsifier may be, for example, a homomixer, a paddle mixer, a Henschel mixer, a homo disper, a colloid mill, a propeller stirring apparatus, a homogenizer, an in-line-type continuous emulsifier, an ultrasonic emulsifier, a vacuum-type frozen mixer, or the like.

Next, the aqueous dispersion of the cross-linkable composition for forming the silicone elastomer particles, prepared using the method described above, is allowed to rest while heating or at room temperature, to cure the cross-linkable silicone rubber composition that is dispersed in the water, enabling preparation of an aqueous dispersion of silicone elastomer particles. When heating the aqueous dispersion of the silicone elastomer particles, preferably the heating temperature is no more than 100° C., and between 1° and 95° C. is particularly preferred. Moreover, the method for heating the cross-linkable silicone rubber composition aqueous dispersion may be, for example, a method wherein the aqueous dispersion is heated directly, a method wherein the aqueous dispersion is added to hot water, or the like. The silicone elastomer particles may be prepared next through removing the water from the aqueous dispersion of the silicone elastomer particles. The method for removing the water from the aqueous dispersion may be, for example, a method that uses a vacuum dryer, a hot air circulating oven, or a spray dryer. Note that the heating/drying temperature of the spray dryer must be set as appropriate based on the thermal durability of the silicone elastomer particles, the cross-linking temperature, and the like. Note that preferably the temperature of the silicone elastomer particles is controlled so as to be no greater than the glass transition temperature thereof, in order to prevent secondary cohesion of the microparticles produced. The silicone elastomer particles obtained in this way may be recovered through a cyclone, a bag filter, or the like.

[Coating with the Silicone Resin]

A distinctive feature of the silicone resin-coated silicone elastomer particles according to the present invention is that the surfaces, in whole or in part, of the silicone elastomer particles prepared through the method described above are coated by a silicone resin structured from siloxane units expressed as $SiO_{4/2}$. Here the siloxane resin used in coating preferably is structured from substantially only siloxane units expressed by $SiO_{4/2}$, where the inclusion proportion of siloxane units other than siloxane units expressed by $SiO_{4/2}$ (specifically, siloxane units expressed by $R_3SiO_{1/2}$, $R_2SiO_{2/2}$, and $RSiO_{3/2}$, where R is a monovalent organic group) must be no greater than 5 mass % in respect to the silicone resin as a whole that is used for coating the silicone elastomer particles, and preferably is less than 3 mass %, and particularly preferably is less than 1 mass %. Most preferably, no component that would provide siloxane units other than siloxane units expressed by $SiO_{4/2}$ is added intentionally, and most preferably no other siloxane units whatsoever are included. If other siloxane units (for example, silsesquioxane resin that is expressed by $RSiO_{3/2}$) were included, there would be a tendency for the silicone resin-coated silicone elastomer particles produced to be scattered as dust during handling, or to adhere to the container, which would result in a negative effect on ease of handling and on efficiency in operations.

Here the silicone resin structured from siloxane units expressed by $SiO_{4/2}$ assumes a polymer structure that is expressed by $[SiO_{4/2}]_n$ (where n is a positive number) wherein the $SiO_{4/2}$ units form a network polymer, increasing the conformity with the surfaces of the silicone elastomer particles, when compared to that of particulate silica or silsesquioxane that is expressed by $RSiO_{3/2}$, and also suppressing the dust and adhesion of the coated particles, and having superior uniform dispersibility into organic resins.

The silicone resin described above can be produced through a hydrolysis reaction of tetraalkoxysilane, or the like, at the silicone elastomer particle surface, or through a hydrolysis reaction, or a dehydration/dealcoholization condensation reaction of a silane compound that provides siloxane units, expressed by $SiO_{4/2}$, through the condensation reaction. Preferably the silane compound that provides the silicone resin described above is a tetraalkoxysilane, and may be, for example, a hydrolysis condensate of a tetraalkoxysilane having one or more selections from alkoxy groups, methoxy groups, ethoxy groups, propoxy groups, and butoxy groups with carbon numbers between 1 and 4, where the use of tetraethoxysilane is particularly preferred. Note that, from the perspective of the technological effects according to the present invention, preferably substantially no silane compounds are included that would provide siloxane units other than siloxane units expressed by $SiO_{4/2}$ accompanying the condensation reaction, and preferably the silane compound is a tetraalkoxysilane alone, and, more preferably, is tetraethoxysilane alone.

While there is no particular limitation on the coating, for the surfaces of the silicone elastomer particles, that uses the silane compound such as the tetraalkoxysilane, it may be produced through hydrolysis condensation of a silane compound, such as a tetraalkoxysilane, or the like, in the presence of the silicone elastomer particles, described above, and an alkaline substance in water to coat the surfaces of the silicone elastomer particles with the silicone resin that is structured from siloxane units that are expressed by $SiO_{4/2}$. Note that the timing with which the alkaline substance or the acidic substance is added is arbitrary, but from the perspective of coating the surfaces of the silicone elastomer particles uniformly, preferably the silane compound, such as the tetraalkoxysilane, or the like, is added gradually into water that includes the silicone elastomer particles and the alkaline substance.

Preferably the addition of the silane compound, such as the tetraalkoxysilane, or the like, is carried out while stirring using a normal stirring device, such as propeller blades, a flat plate, or the like. While the silane compound, such as the tetraalkoxysilane, or the like, may be added all at once, preferably it is added gradually over time. From the perspective of coating the surfaces of the silicone elastomer particles uniformly, preferably the temperature of the aqueous reaction fluid that includes the silicone elastomer particles and the alkaline substance is between 1° and 60° C., and more preferably in a range between 1° and 40° C. If in the temperature range described above, the hydrolysis/condensation reaction of the tetraalkoxysilane will progress gradually at the surfaces of the silicone elastomer particles to coat uniformly with the silicone resin. Note that the stirring of the reaction fluid may be continued until completion of the desired coating reaction through the silicone resin, and, in order to complete the reaction, this may be carried out at a temperature that is higher than the temperature described above (for example, while heating to 40° C. or more).

The alkaline substance or acidic substance acts as a hydrolysis condensation reaction catalyst for the silane compound, such as the tetraalkoxysilane, or the like. In the present invention, an alkaline substance is preferred, which may be used singly or in combination of two or more thereof. The alkaline substance may be added as-is, or may be added after forming into an alkaline aqueous solution. The amount of the alkaline substance added is an amount such that the pH of the aqueous dispersion that includes the alkaline substance, for the aqueous reaction fluid that includes the silicone elastomer particles and the alkaline substance, will be between 10.0 and 13.0, and preferably in a range between 10.5 and 12.5. If outside of this pH range, the coating of the silicone elastomer particles by the silicone resin structured from the siloxane units expressed by $SiO_{4/2}$, derived from the silane compound such as the tetraalkoxysilane, or the like, may end up inadequate.

There is no particular limitation on the alkaline substance, which may use, for example, an alkali metal hydroxide such as potassium hydroxide, sodium hydroxide, lithium hydroxide, or the like; an alkaline earth metal hydroxide such as calcium hydroxide, barium hydroxide, or the like; an alkali metal carbonate such as potassium carbonate, sodium carbonate, or the like; ammonia; a tetraalkyl ammonium hydroxide such as tetramethyl ammonium hydroxide, tetraethyl ammonium hydroxide, or the like; or an amine such as monomethylamine, monoethylamine, monopropylamine, monobutylamine, monopentylamine, dimethylamine, diethylamine, trimethylamine, triethanolamine, ethylenediamine, or the like, where, of these, ammonia is most preferred because it can be removed easily through evaporation from the silicone microparticle powder produced. A commercially available aqueous solution of ammonia may be used for the ammonia.

After the hydrolysis/condensation reaction described above, the silicone resin-coated silicone elastomer particles according to the present invention that have been produced may be used as-is in an aqueous dispersion (aqueous suspension), or, suitably, the water content may be removed from the reaction solution to isolate the silicone resin-coated silicone elastomer particles. The method for removing the water from the aqueous dispersion may be, for example, a method that performs drying through a vacuum dryer, a hot air circulating oven, or a spray dryer. Note that, as a pre-process for these operations, the dispersion may be condensed through a method such as heated spin-drying, separation through filtration, centrifugal separation, decantation, or the like, and, if necessary, the dispersion may be rinsed with water.

In the silicone resin-coated silicone elastomer particle according to the present invention, there is no particular limitation on the amount of coating by the silicone resin; however, preferably the amount of coating by the silicone resin that is structured from siloxane units expressed by $SiO_{4/2}$ is in a range of between 5.0 and 40.0 parts by weight in respect to 100 parts by weight of the silicone elastomer particles, and a range of between 5.0 and 20.0 parts by weight is particularly preferred. If less than the lower limit set forth above, the amount of covering by the silicone resin that is structured from siloxane units expressed by $SiO_{4/2}$ would be inadequate, which could cause the technological effects, such as uniformity of dispersion into the organic resin, to be inadequate. On the other hand, if the amount of coating were greater than the upper limit set forth above, the hard physical properties derived from the silicone resin that is structured from the siloxane units expressed by $SiO_{4/2}$ would have a negative effect on the elasticity from the silicone elastomer particles and on the properties as an elastic body, which could have a negative effect on the feel when mixed into a cosmetic composition or the feel in use, and, when mixed into an organic resin, could reduce the stress relaxation performance, or the like.

The amount of coating by the silicone resin described above can be controlled easily through controlling the amount of the silane compound, such as the tetraalkoxysilane, or the like, for forming the silicone resin that is added to the reaction solution described above.

[Crushing/Grading Operation]

The silicone resin-coated silicone elastomer particles according to the present invention are produced through the method described above, but when the silicone resin-coated silicone elastomer particles produced are condensed through removing the water content, the particles may be, and preferably are, crushed using mechanical force in a pulverizer such as a jet mill, a ball mill, a hammer mill, or the like. Moreover, grading may be carried out using a sieve so as to be of no greater than specific particle diameters. In particular, silicone resin-coated silicone elastomer particles that have agglomerations can be used after crushing using mechanical forces to produce uniformly functional particles that do not include course particles, improving the dispersibility into various types of organic resins, the stress relaxation characteristics, the feel in use when mixed into cosmetics, and the like.

[Average Primary Particle Diameters]

The silicone resin-coated silicone elastomer particles according to the present invention have no particular limitation in the average primary particle diameters thereof, but when an organic resin additive that is added for the purpose of relaxing stress in an organic resin, preferably the average primary particle diameter, measured through a laser diffraction/scattering method, is between 0.5 and 20 μm, and more preferably between 0.5 and 15 μm. Note that the particle diameters of the silicone resin-coated silicone elastomer particles are controlled depending on the silicone elastomer particles prior to coating, the amount of coating, and the crushing/grading step, described above.

[Method for Manufacturing the Silicone Resin-Coated Silicone Elastomer Particles]

The silicone resin-coated silicone elastomer particles according to the present invention can be produced through a method for manufacturing that includes, as described above, performing, on the silicone elastomer particles produced using the aqueous suspension, described above:

Step (II): a step for coating the surfaces of the silicone elastomer particles with a silicone resin that is a hydrolyzate of a tetraalkoxysilane; and Step (III): a step for producing silicone resin-coated silicone elastomer particles that have an average primary particle diameter of between 0.5 and 20 μm, measured through a laser diffraction/scattering method, through using mechanical means to crush the silicone resin-coated silicone elastomer particles (including agglomerations) produced in Step (II). Note that the details for the steps listed above are as described above.

[Organic Resin Additives, Organic Resin, Coating, and Coating Agent]

The silicone resin-coated silicone elastomer particles according to the present invention are superior in uniformity of dispersion into an organic resin, and, if desired, in terms of stress relaxation characteristics, and the like, and remarkably superior in terms of ease of handling due to being resistant to producing dust and adhering to the container during mixing. Moreover, the member, coating film, or coating wherein the organic resin, into which the silicone resin-coated silicone elastomer particles have been mixed, has been cured has flexibility (including softness of the coating layer), durability, adhesion to the substrate, and improved compliance, and, in particular, has superior flexibility, heat resistance, and shock resistance, and thus is extremely useful as a highly functional organic resin, coating, or coating agent used in electronic materials.

[Organic Resin]

The organic resin that includes the silicone resin-coated silicone elastomer particles according to the present invention preferably is a curable organic resin composition or thermoplastic resin. Of these, the curable resin is suitable as an electronic material such as a semiconductor substrate, or the like. More specifically, the curable organic resin composition may be, for example, a phenol resin, a formaldehyde resin, a xylene resin, a xylene-formaldehyde resin, a ketone-formaldehyde resin, a furon resin, a urea resin, an imide resin, a melamine resin, an alkyd resin, an unsaturated polyester resin, an aniline resin, a sulfone-amide resin, a silicone resin, an epoxy resin, or a copolymerized resin of these resins. These curable resins may be used in combination of two or more of the above. In particular, the cured resin preferably is one or more selections from a group comprising epoxy resins, phenol resins, imide resins, and silicone resins. The epoxy resin should be a compound that includes a glycidyl group or an alicyclic epoxy group and may be, for example, an o-cresol novolac-type epoxy resin, a phenol novolac-type epoxy resin, a biphenyl-type epoxy resin, a bisphenol A-type epoxy resin, a bisphenol F-type epoxy resin, a dicyclopentadiene-type epoxy resin, a naphthalene-type epoxy resin, an anthracene-type epoxy resin, a naphthol aralkyl-type epoxy resin, a polyvinylphenol-type epoxy resin, a diphenylmethane-type epoxy resin, a diphenylsulfone-type epoxy resin, a triphenolalkane-type epoxy resin, a cresol/naphthol co-condensation-type epoxy resin, a bisphenylethylene-type epoxy resin, a fluorene-type epoxy resin, a stilbene-type epoxy resin, a spirocoumarone-type epoxy resin, a norbornene-type epoxy resin, a terpene-type epoxy resin, a phenol cyclohexane-type epoxy resin, a halogenated epoxy resin, an imide group-containing epoxy resin, a maleimide group-containing epoxy resin, an allyl group-modified epoxy resin, a silicone-modified epoxy resin, or the like. Moreover, the phenol resin may be of a polyvinylphenol type, a phenol novolac type, a naphthol type, a terpene type, a phenol dicyclopentadiene type, a phenol aralkyl type, a naphthol aralkyl type, a triphenol alkane type, a dicyclopentadiene type, a cresol/naphthol co-condensation type, a xylene/naphthol co-condensation type, or the like. Furthermore, the silicone resin may be an epoxy-modified silicone resin wherein an epoxy resin has been reacted with the silanol groups or silicon atom-bound alkoxy groups in a silicone resin. The curing mechanism for such a curable resin may be that of a thermally curable type, an energy beam curable type through ultraviolet light, radiation, or the like, a moisture curable type, a condensation reaction curable type, an addition reaction curable type, or the like. Moreover, while there is no particular limitation on the characteristics of such a curable resin at 25° C., preferably it is either a liquid or a solid that is softened through heating.

As other arbitrary components, a curing agent, a curing accelerating agent, a filling agent, a light sensitizing agent, a high-level fatty acid metal salt, an ester-based wax, a plasticizing agent, and the like, can be mixed into the organic resin that includes the silicone resin-coated silicone elastomer particles according to the present invention. The curing agent may be: an organic acid such as carboxylic acid, sulfonic acid, or the like, or an anhydride thereof; an organic hydroxy compound; an organic silicon compound that has a silanol group, an alkoxy group, or a halogen group; a primary or secondary amino compound; or the like, and may be a combination of two or more of the above. Moreover, the curing accelerating agent may be: an organic metal compound such as a tertiary amine compound, aluminum, zirconium, or the like; an organic phosphorus compound such as phosphine, or the like; or a heterocyclic amine compound, a boron complex compound, an organic ammonium salt, an organic sulfonium salt, an organic peroxide, or a hydrosilylation catalyst. Additionally, the filling agent may be, for example: a fibrous filling agent such as glass fibers, asbestos, alumina fibers, ceramic fibers that have alumina and silica as components thereof, boron fibers, zirconia fibers, silicon carbide fibers, metal fibers, polyester fibers, aramid fibers, nylon fibers, phenol fibers, natural animal or vegetable fibers, and the like; powderous filling agents such as melted silica, precipitated silica, fumed silica, calcinated silica, zinc oxide, calcinated clay, carbon black, glass beads, alumina, talc, calcium carbonate, clay, aluminum hydroxide, barium sulfate, titanium dioxide, aluminum nitride, silicon carbide, magnesium oxide, beryllium oxide, kaolin, mica, zirconia, and the like; and so forth, where two or more of the above may be combined for use. For an epoxy-based resin, the inclusion of an amine-based curing agent is particularly preferred.

The silicone resin-coated silicone elastomer particles according to the present invention may be mixed in as an additive in a thermoplastic resin other than those which are described above, and can be used as an agent for modifying a physical characteristic, such as a surface lubricant, a stress relaxing agent, or the like, or an agent for modifying an optical characteristic, such as a light scattering agent, or the like. There is no particular limitation on the type of thermoplastic resin, which may be at least one polymer selected from a group comprising, for example, polycarbonate-based resins, polyester-based resin, polyether-based resins, polylactic acid-based resins, polyethylenes, polypropylenes, polyolefin-based resins such as ethylene-propylene-based copolymers, or the like, polystyrene-based resins, styrene-based copolymers, fluorine-based polymers such as tetrafluoroethylene, or the like, polyvinyl ethers, and cellulose-based polymers, or a composite resin that combines the above. The silicone resin-coated silicone elastomer particles according to the present invention can be dispersed uniformly, using a mixing machine such as a two-axis or one-axis extruder, or a metered mixer, into these thermoplastic resins (including master batches thereof), and can be molded for use into the desired form, such as into the shape of a film.

The amount of the silicone resin-coated silicone elastomer particles added can be selected as appropriate depending on the physical properties desired in the organic resin, but generally is in a range of between 0.1 and 30 parts by weight in respect to 100 parts by weight of the organic resin, and should be between 0.5 and 10 parts by weight. This is because if the amount of the particles added were less than the lower limit set forth above, the performance such as in the stress relaxation characteristics in respect to the resin, or the like, may be inadequate, which would reduce the flexibility, heat resistance, and shock durability of the organic resin cured material produced, and, in particular, because of the tendency for there to be reduced heat resistance and shock durability after absorbing moisture. On the other hand, this is because if greater than the upper limit set forth above, there would not only be a negative effect on the ease of handling given that the organic resin, coating, or coating agent would thicken after mixing, but also because of the tendency toward a negative effect on the mechanical characteristics of the organic resin cured material produced.

If the silicone resin-coated silicone elastomer particles according to the present invention are mixed into an organic resin, the stress relaxation effects will be superior, enabling mixing into an epoxy resin, or the like, for a printed circuit board to form pre-preg, and, additionally, a copper foil with a resin layer that includes filler particles, for a printed circuit board, equipped with a resin layer that includes the silicone resin-coated silicone elastomer particles according to the present invention on one face of a copper foil may be formed, enabling use in a copper clad laminate (CCL) application.

[Coating and Coating Agent]

The coating/coating agent that includes the silicone resin-coated silicone elastomer particles according to the present invention may be, for example, of a room temperature curable type, a room temperature drying type, or a heated curable type, and, depending on the characteristics thereof, may be aqueous, oily, or powdery, and further, depending on the resin that is the vehicle, may be, for example, a polyurethane resin coating, a butyral resin coating, a long-oil phthalic acid resin coating, an alkyd resin coating, an amino-alkyd resin coating made from an amino resin and an alkyd resin, an epoxy resin coating, an acrylic resin coating, a phenol resin coating, a silicone-modified epoxy resin coating, a silicone-modified polyester resin coating, a silicone resin coating, or the like.

The amount of silicone resin-coated silicone elastomer particles according to the present invention that are added may be selected appropriately depending on the physical properties desired in the coating or coating agent, but in order to apply a soft delustered nature uniformly to the coating film that is produced, preferably it is in a range of between 0.1 and 150 parts by weight in respect to 100 parts by weight of the solid content of the coating, and more preferably in a range between 0.1 and 100 parts by weight, and particularly in a range between 0.1 and 50 parts by weight, or between 0.1 and 20 parts by weight. If the amount of particles added were less than the lower limit set forth above, there would be inadequate performance such as the delustering performance in the coating film, adhesion, stress relaxing performance, and the like, and if greater than the upper limits set forth above, the organic resin, coating, or coating agent would thicken after mixing, which would have a negative effect on the ease of handling.

The coating or coating agent that includes the silicone resin-coated silicone elastomer particles according to the present invention may include: alcohols such as methanol, ethanol, and the like; ketones such as methyl ethyl ketone, methyl isobutyl ketone, and the like; esters such as ethyl acetate, butyl acetate, cellosolve acetate, and the like; amides such as N,N-dimethyl formamide; olefins such as hexane, heptane, octane, and the like; organic solvents such as aromatic hydrocarbons such as toluene, xylene, and the like; known inorganic filling agents such as reinforced silica, and the like, organic filling agents, curing accelerating agents, silane coupling agents, pigments such as carbon black, dyes, oxidation inhibitors, thickening agents made from polymer compounds, flame retardant agents, and weather durability bestowing agents.

[Cosmetic Composition]

The silicone resin-coated silicone elastomer particles according to the present invention are useful as cosmetic raw materials, and because the surfaces thereof are coated, in whole or in part, with a silicone resin that is structured from siloxane units that are expressed by $SiO_{4/2}$, the uniformity of dispersion into other cosmetic raw materials (and particularly oily raw materials) and oil absorbing characteristics are superior to those of conventional known silicone elastomer particles and silicone composite particles, and when applied to the skin or hair, there are the benefits of preventing an oily or sticky feel in the cosmetics, the ability to spread smoothly, application of a soft feel, and having a superior feel in use. Moreover, the silicone resin-coated silicone elastomer particles according to the present invention are resistant to scattering as dust, and resistant to adhering to the container, and thus are superior in terms of ease of handling and mixture stability.

While there are no particular limitations on the types of cosmetic compositions that include the silicone resin-coated silicone elastomer particles according to the present invention, they may be, for example: cosmetics for cleaning, such as soaps, body washes, cleansing creams, and the like; base cosmetics such as skin lotions, creams and milky lotions, packs, and the like; base makeup cosmetics such as face powders, foundations, and the like; facial cosmetics such as lipsticks, blushes, eyeshadows, eyeliners, mascaras, and the like; makeup cosmetics such as nail polishes, and the like; hair cosmetics such as hair rinses, hairstyling agents, hair restoring agents, hair conditioning agents, hair dyes, and the like; fragrant cosmetics such as perfumes, colognes, and the like; toothpastes; bath products; or specialty cosmetics such as depilatory agents, shaving lotions, antiperspirants/deodorizing agents, sun blocks, and the like. Moreover, the forms of these cosmetic compositions may be, for example, aqueous liquids, oily liquids, emulsions, creams, foams, semi-solid shapes, solid shapes, powdery, or the like. Moreover, these cosmetic compositions may be used as sprays.

In these cosmetic compositions, the inclusion proportions of the silicone resin-coated silicone elastomer particles described above preferably are in a range of between 0.5 and 99.0 mass % in the cosmetic compositions, and particularly preferably in a range between 1.0 and 95 mass %. This is because if the inclusion proportion of the silicone resin-coated silicone elastomer particles were in excess of the upper limit of the range described above, the effect as a cosmetic would be lost, and if less than the lower limit of the range described above, there would be little improvement in the feeling of the cosmetic composition in use.

The silicone resin-coated silicone elastomer particles according to the present invention may be used to replace some or all of the silicone-based particles for the silicone particles (silicone rubber powders, or the like) or cosmetic compositions that include silicone compound particles (and, particularly in the examples of preparations) proposed in Patent Document 2 (Japanese Unexamined Patent Application Publication 2011-105663), Patent Document 3 (Japanese Unexamined Patent Application Publication 2011-168634), Patent Document 4 (Japanese Unexamined Patent Application Publication 2011-102354), Patent Document 5 (International Patent Application Publication WO 2017/191798) and Japanese Unexamined Patent Application Publication 2014-122316, which may further improve the feeling in use of the cosmetic compositions, and the production efficiency thereof, proposed in these patent documents.

Moreover, the silicone resin-coated silicone elastomer particles according to the present invention may be applied in replacing some or all of the silicone-based particles in the applications and preparations of cosmetic compositions disclosed in the patent documents described above, and these uses are also included in the scope of the invention in the present application. Moreover, the silicone resin-coated silicone elastic particles according to the present invention may be, and preferably are, combined with arbitrary components such as: the cosmetic media (aqueous media or oily media) disclosed in the cosmetic composition disclosed in the patent documents disclosed above, oily media (including oil agents and volatile oil agents), water, coloring agents, alcohols, water-soluble polymers, film-forming agents, oil agents, oil-soluble gelling agents, organically modified clay minerals, surface activating agents, resins, salts, moisture retaining agents, preservatives, antibacterial agents, antioxidants, pH adjusters, chelating agents, cooling agents, anti-inflammatory agents, components for skin beautification (whitening agents, cell activating agents, skin roughening agents, blood circulation promoting agents, skin astringents, anti-seborrheic agents, etc.), vitamins, amino acids, nucleic acids, hormones, clathrates and the like, physiologically active substances, pharmaceutically active ingredients, and fragrances, and the like.

In particular, the silicone resin-coated silicone elastomer particles according to the present invention can achieve a particularly ideal feel in use in cosmetic compositions and preparations including, in particular, cosmetic compositions that include oily cosmetic raw materials such as oils, or the like, due to oil absorption that is superior to that of conventional known silicone particles or silicone composite particles that are coated with silsesquioxane.

In manufacturing a cosmetic according to the present invention, the cosmetic raw material according to the present invention, as described above, can be mixed uniformly with other cosmetic raw materials easily, enabling easier manufacturing. The various types of mixing equipment and kneading equipment normally used in manufacturing of cosmetics may be used as the mixing means. The device may be, for example, a homomixer, a paddle mixer, a Henschel mixer, a homo disper, a colloid mixer, a propeller stirring apparatus, a homogenizer, an in-line-type continuous emulsifier, an ultrasonic emulsifier, a vacuum-type frozen mixer, or the like.

EMBODIMENTS

Silicone resin-coated silicone elastomer particles and manufacturing methods thereof according to the present invention will be explained in more detail using embodiments and reference examples. However, the present invention is not limited to these embodiments. Viscosities in the embodiments are values at 25° C. Moreover, the characteristics of the individual silicone particles are measured as below. Note that in the embodiments, unless otherwise noted, "silicone particle" is a general term for a particle comprising a silicone cured material (a cured silicone particle), and does not include emulsions.

[JIS a Hardness of the Silicone Particles]

The curable silicone compositions that are the raw materials for the silicone elastomer particles were heated for 150° C. for one hour in a heating oven and cured into sheet shapes, and the hardnesses thereof were measured by a JIS A hardness meter specified in JIS K 6253.

[Amount of Residual SiH in the Silicone Particles]

An ethanol solution of potassium hydroxide with a density of 40%, in respect to a unit mass, was added to the cured silicone particles and allowed to rest for one hour, and hydrogen gas produced up until the reaction end point was reached was trapped, and through headspace gas chromatography, the amount of trapped hydrogen produced was measured, to measure the per-unit mass amount of remaining silicon atom-bound hydrogen atoms. The amount of remaining silicon atom-bound hydrogen atoms in the silicone elastomer particles used in the present invention was 100 ppm (for all cases).

[Average Primary Particle Diameters of the Emulsion Particles]

The emulsions, prior to addition of the platinum catalyst, were measured through a laser diffraction-type grain size distribution measuring instrument (LS-230, manufactured by Beckman Coulter), and the median diameter (the "50% particle size," which is the particle size corresponding to 50% in the cumulative distribution) was defined as the average particle size.

[Average Primary Particle Diameter of the Silicone Particles (Powder)]

With ethanol as the dispersing agent, the particle sizes of the cured silicone particles were measured using a laser diffraction-type grain-size distribution measuring instrument (LA-500, by Horiba, Ltd.), to produce values for the median diameter of the cured silicone particles in the ethanol (D90, in micrometer, which is the particle size corresponding to 50% in the cumulative distribution), and the arithmetic deviation (SD, in $\mu m^2$), which indicates the variation in the particle size distribution. For the measurement samples, cured silicone particles (1 g) and ethanol (100 mL) were dispersed in a 300-mL cup using a stirring blade and ultrasonic vibration equipment.

[Method for Measuring the Quantity of Oil Absorbed by the Powder]

1 g of cured silicone particles was placed in a 100-mL beaker, and methyl ethyl ketone (MEK) was dripped in, one drop at a time, while stirring the silicone particles slowly with a glass rod, and the volume of oil drips required to form a uniform paste of cured silicone particles and oil was calculated. The proportion of the volume of the oil dripped, in respect to the cured silicone particles, was defined as the quantity of oil absorbed (percent by weight).

[Uniformity of Dispersion into the Epoxy Resin Solution]

2.87 g of silicone particles were added to 50 g of a curable epoxy resin solution (solids content: 57.4%), and rotated for 10 minutes in a ball mill frame, and 30 minutes thereafter the uniformity of dispersion was evaluated as "1," "3," or "5," using the standards, below, based on the external appearance.

Note that the curable epoxy resin solution was prepared using the formulation below:

Brominated bisphenol A epoxy resin (Brand name "jER5046B80," manufactured by Mitsubishi Chemical): 140 g Novalac-type epoxy resin (brand name "jER154," manufactured by Mitsubishi Chemical): 40 g 2-butanone: 30 g 2-methoxy ethanol: 50 g Dicyandiamide: 5.5 g 2-ethyl-4-methyl imidazole: 0.1 g 5: A state was maintained wherein the cured silicone particles were dispersed uniformly into the epoxy resin solution.

3: While during the operation for dispersing using mechanical strength the cured silicone particles were dispersed uniformly into the epoxy resin solution, separation was observed after resting for 30 minutes.

1: The cured silicone particles could not be dispersed uniformly into the epoxy resin solution.

[Epoxy Resin Stress Relaxation Performance Evaluation]

After a glass fabric was dipped into the epoxy resin solution described above (cured silicone particles solids content: 10 mass %), it was dried in an oven at 100° C. The semi-solid fiberglass-epoxy resin composition produced was pressed at 175° C. for 60 minutes at 100 kg/cm$^2$, to produce a cured fiberglass-epoxy resin molding with a thickness of 0.4 mm. A strip-shaped test piece of 40 mm×10 mm×0.4 mm was formed from the molding that was produced, and a torsional stress relaxation test was performed with a 0.1% deformation.

In this case, the initial torsional stress of the fiberglass-epoxy molded product that did not include the cured silicone particles was 6.82 GPa, and the stress relaxation performance was evaluated using the standards below. Superiority in stress relaxation performance given addition of identical amounts of cured silicone particles is indicated in the sequence of A, B, and C.

A: Initial torsional stress is less than 5.75 GPa.
B: Initial torsional stress is in the range between 5.75 and 6.50 GPa.
C: Initial torsional stress is greater than 6.50 GPa.

[Scatterability (%)]

A model PT-X Powder Tester (manufactured by Hosokawa Micrometer) was used to measure the weight of cured silicone particles that fell into a tray with a diameter of 10 cm that was placed directly below when 10 g of cured silicone particles was dropped from a height of 60 cm through a hole with a diameter of 5 cm. The scatterability of the cured silicone particles was measured based on the mass using the formula below:

Scatterability (%)=(10 (g)−(weight (g) of the powder on the tray))/10 (g)×100

Note that the greater the amount of cured silicone particles that dropped to the outside of the tray (=10 (g)−(weight (g) of powder on the tray)), the more readily the cured silicone particles scatter, with the evaluation that the ease of handling is worse.

The average formulas for components of (A) and component (B) used in the embodiments and reference examples are listed below.

In the formulas below, Vi indicates a vinyl group that is expressed as $CH_2=CH-$, "Me" indicates a methyl group that is expressed by $CH_3-$, and "He" indicates a hexenyl group that is expressed by $CH_2=CH-CH_4H_8-$.

[Chemical Formula 1-1]

Alkenyl group inclusion proportion: 2.7 wt %. Viscosity: 100 mPa·s.

[Chemical Formula 1-2]

Alkenyl group inclusion proportion: 0.97 wt %. Viscosity: 420 mPa·s.

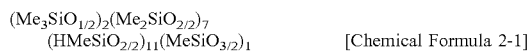
[Chemical Formula 2-1]

Silicon atom-bonded hydrogen atom inclusion proportion: 0.825 wt %. Viscosity: 15 mPa·s.

[Chemical Formula 2-2]

Silicon atom-bonded hydrogen atom inclusion proportion: 0.015 wt %. Viscosity: 500 mPa·s.

Preparation Example 1: Example of Preparation of Silicone Elastomer Particles Using Polyorganosiloxane that Includes Hexenyl Groups (Aqueous Suspension Method)

Polyorganosiloxane expressed by the average formula of [Chemical Formula 1-1] and polyorganosiloxane expressed by the average formula of [Chemical Formula 2-1] were mixed uniformly with a mass ratio of 89:11 at room temperature. Following this, the composition was dispersed into an aqueous solution at 25° C. made from 3.0 parts by weight of polyoxyethylene alkyl (C12-14) ether and 20 parts by weight purified water, and following uniform emulsification using a colloid mill, this was diluted through adding 350 parts by weight purified water, to prepare an emulsion. Next, an isopropyl alcohol solution of chloroplatinic acid (in an amount such that the platinum metal in the composition will be 10 ppm, in terms of mass) was formed into an aqueous solution, with polyoxyethylene alkyl (C12 through 14) ether, and in a pure form, and added to the emulsion, and after stirring, the emulsion was allowed to rest for three hours at 50° C., to prepare a uniform aqueous suspension of the silicone rubber particles. Following this, the aqueous solution was dried using a small spray dryer (manufactured by Ashizawa-Niro), to produce silicone elastomer particles. The JIS A hardness of the silicone elastomer particles produced was 68, and the average primary particle diameter thereof was 2.3 μm.

Embodiment 1

500 g of the silicone elastomer particle aqueous dispersion produced in Preparation Example 1 was transferred to a glass flask with a capacity of two liters that was provided with a stirring device equipped with a stirring blade, and 500 g of water and 20 g of 28% of aqueous ammonia were added. The pH of the fluid in this case was 11. After adjusting the temperature to between 5 and 10° C., 52 g of tetraethoxysilane (an amount that produces 15 parts by weight, in respect to 100 parts by weight of the silicone elastomer particles prior to coating with the silicone resin that is structured from siloxane units expressed by $SiO_{4/2}$, after the hydrolysis/condensation reaction) was dripped over 30 minutes, and then stirred for an additional hour. During this time, the liquid temperature was maintained at between 5 and 10° C. Following this, heating was performed to between 55 and 60° C., and while still maintaining the temperature, stirring was carried out for another hour, to complete the hydrolysis/condensation reaction of the tetraethoxysilane.

The hydrolysis/condensation reaction fluid of the silicone elastomer particles/tetraethoxysilane that was produced was filtered. The dewetted material was transferred to a stainless steel tray, and dried to a temperature of 105° C. in a hot air circulating dryer, and the dried material was crushed in a jet mill, to produce microparticles that have fluidity. When these microparticles were observed in an electron microscope, they were spheroidal particles where the particle surfaces were coated with silicone resin; it was confirmed that they had become silicone resin-coated silicone elastomer particles coated with a silicone resin structured from siloxane units expressed by $SiO_{4/2}$. The average primary particle diameter of the silicone resin-coated silicone elastomer particles produced was 5.3 μm.

Moreover, the silicone resin-coated silicone elastomer particles produced in Embodiment 1 were observed using a scanning electron microscope (SEM) (device name: Model S-3400N, manufactured by Hitachi High-Technologies), the image of which is shown in FIG. 1.

<SEM Conditions>
Vacuum Level: <1 Pa
Acceleration Voltage: 10.0 kV
Probe Current: 30 μA Embodiment 2

In the same manner as in Embodiment 1, except for dripping 34.9 g of tetraethoxysilane (in an amount so as to be 10 parts by weight, in respect to 100 parts by weight of the silicone elastomer particles prior to coating, of the silicone resin that is structured from siloxane units that are expressed by $SiO_{4/2}$ after the hydrolysis/condensation reaction) having been dripped over 30 minutes, it was confirmed that silicone resin-coated silicone elastomer particles having surfaces coated with silicone resins structured from siloxane units expressed by $SiO_{4/2}$ were produced. The average primary particle diameter of the silicone resin-coated silicone elastomer particles produced was 6.5 μm.

Reference Example 1

The silicone elastomer particles produced in Preparation Example 1 were evaluated as-is.

Reference Example 2

Silicone elastomer particles with surfaces coated with silsesquioxane were produced in the same manner as in Embodiment 1, except for replacing the 34.9 g of tetraethoxysilane with dripping 20.34 g of methyl trimethoxy silane (an amount such that the silsesquioxane resin expressed by $MeSiO_{3/2}$, after the hydrolysis/condensation reaction, will be 10 mass % in respect to the particles after coating) over 30 minutes. The average particle diameter thereof was 2.7 μm.

For embodiments 1 and 2 and Reference Examples 1 and 2, the characteristics are shown in Table 1.

TABLE

|  | Oil Absorbency (MEK) g | Uniformity of Dispersion into Epoxy Resin Solution | Stress Relaxation Characteristics | Scattering (%) | Average Primary Particle Diameter (μm) |
|---|---|---|---|---|---|
| Embodiment 1 | 2.31 | 5 | A | 32 | 5.3 |
| Embodiment 2 | 1.95 | 3 | A | 38 | 6.5 |
| Reference Example 1 | 1.16 | 1 | B | 15 | 2.3 |
| Reference Example 2 | 123 | 5 | B | 43 | 2.7 |

Examples of preparations of cosmetics according to the present invention, in which the silicone particles that are one form of the present invention can be mixed, are presented below. The present invention is not limited thereto, however.

Embodiment 3: Face Powder

A commercially available product, "Chifure Face Powder N" (manufactured by Chifure Cosmetic Co.) and the silicone resin-coated silicone elastomer particles of Embodiment 1 were mixed uniformly with a 90:10 mass ratio to prepare a face powder, and feel in use of the face powder N (product with the addition) and the face powder N without the addition were subjected to a comparison evaluation by a panel.
[Evaluation Results]
The face powder N to which the silicone resin-coated silicone elastomer particles according to the first embodiment were added, when compared to the case wherein they were not added, was evaluated as being softer, with no feeling of friction, as having a smooth feeling on the skin, and was spread more smoothly. Moreover, when compared to the case wherein they were not added, there was less of a tendency for discoloration of the cosmetic at the time of use, and the evaluation was that of having an overall superiority in field of use.
[Example of Preparation]
The silicone resin-coated silicone elastomer particles according to the present invention may be used to replace some or all of the silicone-based particles for the silicone particles (silicone rubber powders, or the like) or cosmetic compositions that include silicone compound particles (and, particularly in the examples of preparations) proposed in Patent Document 2 (Japanese Unexamined Patent Application Publication 2011-105663), Patent Document 3 (Japanese Unexamined Patent Application Publication 2011-168634), Patent Document 4 (Japanese Unexamined Patent Application Publication 2011-102354), Patent Document 5 (International Patent Application Publication WO 2017/191798) and Japanese Unexamined Patent Application Publication 2014-122316.

Preparation Example 2: Example of Preparation of Silicone Elastomer Particles Using Polyorganosiloxane that Includes Hexenyl Groups (Aqueous Suspension Method)

Polyorganosiloxane expressed by the average formula of [Chemical Formula 1-2] and polyorganosiloxane expressed by the average formula of [Chemical Formula 2-2] were mixed uniformly with a mass ratio of 30:70 at room temperature. Following this, the composition was dispersed into an aqueous solution at 25° C. made from 0.4 parts by weight of polyoxyethylene alkyl (C12-14) ether and 50 parts by weight purified water, and following uniform emulsification using a colloid mill, this was diluted through adding 350 parts by weight purified water, to prepare an emulsion. Next, an isopropyl alcohol solution of chloroplatinic acid (in an amount such that the platinum metal in the composition will be 10 ppm, in terms of mass) was formed into an aqueous solution, with polyoxyethylene alkyl (C12 through 14) ether, and in a pure form, and added to the emulsion, and after stirring, the emulsion was allowed to rest for three hours at 50° C., to prepare a uniform aqueous suspension of the silicone rubber particles. Following this, the aqueous solution was dried using a small spray dryer (manufactured by Ashizawa-Niro), to produce silicone elastomer particles. The JIS A hardness of the silicone elastomer particles produced was 10, and the average primary particle diameter thereof was 7.9 μm.

Embodiment 4

Silicone elastomer particles with surfaces coated with the silicone resin expressed by $SiO_{4/2}$ were produced in the same manner as in Embodiment 1, except for using the silicone elastomer particle aqueous dispersion prepared in Preparation Example 2 instead of the silicon elastomer particle aqueous solution prepared in Preparation Example 1 and dripping 17.4 g of methyl triethoxy silane (an amount such that the silicone resin expressed by $SiO_{4/2}$, after the hydrolysis/condensation reaction, will be 5 parts by mass in respect to 100 parts by mass of the silicone elastomer particles prior coating) over 30 minutes. Using an electron microscope, a structure was confirmed wherein the surfaces of the silicone elastomer particles (JIS-A hardness 10) were coated with the silicone resin in the same way as in Embodiment 1.

APPLICABILITY IN INDUSTRY

The silicone resin-coated silicone elastomer particles according to the present invention are superior in uniformity of dispersion into organic resins, oily raw materials, and the like, and thus can be mixed easily as an additive, and are superior also in stress relaxation performance, if desired, and not prone to scattering at the time of mixing, and resistant to adhering to the container, and thus useful as an organic resin additive for the curable organic resins described above (semiconductor materials, coatings and coating agents, and the like). Moreover, the silicone resin-coated silicone elastomer particles according to the present invention can improve the feel when used as a cosmetic raw material that is mixed into a cosmetic, thus enabling use in skin cosmetics, makeup cosmetics, and the like. Moreover, taking advantage of the physical properties thereof, the silicone resin-coated silicone elastomer particles according to the present invention can be used also as an additive for thermally curable resin compositions, thermoplastic resin compositions, and the like, as an application for electronic materials, or as a surface lubricant for plastic films, or the like.

The invention claimed is:

1. A silicone resin-coated silicone elastomer particle having a structure wherein at least two silicon atoms in a silicone elastomer particle are cross-linked through a silalkylene group with a carbon number between 4 and 20 and where at least some or all of the surface thereof is coated with a silicone resin comprising siloxane units expressed by $SiO_{4/2}$ and wherein the inclusion proportion of silicon atom-bound hydrogen is no greater than 300 ppm, per unit mass.

2. The silicone resin-coated silicone elastomer particle as set forth in claim 1, wherein the amount of coating by the silicone resin is in a range of between 5.0 and 40.0 parts by weight with respect to 100 parts by weight of the silicone elastomer particle.

3. The silicone resin-coated silicone elastomer particle as set forth in claim 1, wherein the average primary particle diameter measured through a laser diffraction/scattering method is between 0.5 and 20 m.

4. The silicone resin-coated silicone elastomer particle as set forth in claim 1, wherein the JIS-A hardness that is measured for the silicone elastomer particles in a state wherein they are not coated with the silicone resin, through curing, in a sheet shape, a cross-linkable composition for forming the silicone elastomer particles, prior to curing thereof is in a range between 10 and 80.

5. The silicone resin-coated silicone elastomer particle as set forth in claim 1, wherein the silalkylene groups included in the silicone elastomer particles are substantially only silalkylene groups with carbon numbers of between 4 and 8, where the inclusion proportion of silalkylene groups with carbon numbers of 3 and below is less than 5 mass % with respect to the silicone elastomer particle.

6. The silicone resin-coated silicone elastomer particle as set forth in claim 1, wherein the silicone resin of the silicone elastomer particle surface is made up substantially from a hydrosilate of a tetraalkoxysilane where the inclusion proportion of siloxane units other than siloxane units expressed by $SiO_{4/2}$ is less than 5 mass % with respect to the silicone resin.

7. The silicone resin-coated silicone elastomer particle as set forth in claim 1, wherein the inclusion proportion of silicon atom-bound hydrogen is no greater than 100 ppm, per unit mass.

8. The silicone resin-coated silicone elastomer particle as set forth in claim 1, wherein a cross-linkable composition for forming a silicone elastomer particle, prior to curing thereof, for a silicone elastomer particle in a state wherein it is not coated with silicone resin, is a cross-linkable composition that comprises:
  (a) an organopolysiloxane having at least two alkenyl groups, with a carbon number between 4 and 20, per molecule;
  (b) an organohydrogen polysiloxane having at least two silicon atom-bound hydrogen atoms per molecule; and
  (c) a hydrosilylation reaction catalyst;
    wherein the mole ratio of the alkenyl group inclusion proportion (Alk) of component (a) and the silicon atom-bound hydrogen atom inclusion proportion (H) of component (b) is in a range of 0.7 through 1.2 (H/Alk).

9. An organic resin additive that includes the silicone resin-coated silicone elastomer particle as set forth in claim 1.

10. An organic resin that includes the silicone resin-coated silicone elastomer particle as set forth in claim 1.

11. A curable organic resin composition that includes the silicone resin-coated silicone elastomer particle as set forth in claim 1.

12. A coating composition or coating agent that includes the silicone resin-coated silicone elastomer particle as set forth in claim 1.

13. A cosmetic preparation that includes the silicone resin-coated silicone elastomer particle as set forth in claim 1.

14. A method for manufacturing the silicone resin-coated silicone elastomer particle as set forth in claim 1, said method comprising:
  preparing a cross-linkable composition comprising:
  (a) an organopolysiloxane having at least two alkenyl groups, with a carbon number between 4 and 20, per molecule;
  (b) an organohydrogen polysiloxane having at least two silicon atom-bound hydrogen atoms per molecule; and
  (c) a hydrosilylation reaction catalyst;
    wherein the mole ratio of the alkenyl group inclusion proportion (Alk) of component (a) and the silicon atom-bound hydrogen atom inclusion proportion (H) of component (b) is in a range of 0.7 through 1.2 (H/Alk);
  emulsifying the cross-linkable composition in water, and curing in the presence of component (c) to produce a spheroidal silicone elastomer particle;
  coating a surface of the spheroidal silicone elastomer particle with a silicone resin that is a hydrolysate of a tetraalkoxysilane; and
  mechanically crushing the silicone resin-coated silicone elastomer particles, and optionally agglomerations thereof, to produce silicone resin-coated silicone elastomer particles with an average primary particle diameter of between 0.5 and 20 m, measured through a laser diffraction/scattering method.

15. The silicone resin-coated silicone elastomer particle as set forth in claim 8, wherein the silicone resin of the silicone elastomer particle surface is made up substantially from a hydrosilate of a tetraalkoxysilane where the inclusion proportion of siloxane units other than siloxane units expressed by $SiO_{4/2}$ is less than 5 mass % with respect to the silicone resin.

16. The silicone resin-coated silicone elastomer particle as set forth in claim 15, wherein the silicone resin is made up only from the hydrosilate of the tetraalkoxysilane.

17. The silicone resin-coated silicone elastomer particle as set forth in claim 1, wherein the silicone resin is made up only from the hydrosilate of the tetraalkoxysilane.

18. The silicone resin-coated silicone elastomer particle as set forth in claim 1, wherein
   the silicone resin has a polymer structure that is expressed by $[SiO_{4/2}]_n$ where n is a positive number and wherein the $SiO_{4/2}$ units form a network polymer.

19. The silicone resin-coated silicone elastomer particle as set forth in claim 1, wherein the silicone resin is in the form of a polymeric coating layer on the surface of the silicone elastomer particle.

\* \* \* \* \*